US009862663B2

(12) United States Patent
Thevasahayam (10) Patent No.: US 9,862,663 B2
(45) Date of Patent: Jan. 9, 2018

(54) METHODS, MATERIALS, AND SYSTEMS FOR CONVERTING ORGANIC ACIDS TO ALCOHOLS

(71) Applicant: EMPIRE TECHNOLOGY DEVELOPMENT LLC, Wilmington, DE (US)

(72) Inventor: Arockiadoss Thevasahayam, Tamilnadu (IN)

(73) Assignee: Empire Technology Development LLC, Wilmington, DE (US)

( * ) Notice: Subject to any disclaimer, the term of this patent is extended or adjusted under 35 U.S.C. 154(b) by 253 days.

(21) Appl. No.: 14/640,465

(22) Filed: Mar. 6, 2015

(65) Prior Publication Data

US 2015/0251981 A1 Sep. 10, 2015

(30) Foreign Application Priority Data

Mar. 6, 2014 (IN) .......................... 1154/CHE/2014

(51) Int. Cl.
*C07C 29/147* (2006.01)
*B01J 19/08* (2006.01)
(Continued)

(52) U.S. Cl.
CPC ......... *C07C 29/147* (2013.01); *B01J 19/0093* (2013.01); *B01J 19/087* (2013.01);
(Continued)

(58) Field of Classification Search
CPC .... B01J 19/0093; B01J 23/78; B01J 35/0033; B01J 19/087; B01J 2219/00961; B01J 2219/00952; B01J 2219/1945; B01J 2219/0892; B01J 2219/0093; B01J 2219/0869; B01J 2219/00909; B01J 2219/00905; B01J 2219/0866; B01J 2219/00799; B01J 2219/00963; B01J 2219/00792; B01J 2219/00835; B01J 2219/00846; B01J 2219/0854; B01J 2219/0877; C07C 29/147; C07C 29/00;
(Continued)

(56) References Cited

U.S. PATENT DOCUMENTS 2,352,791 A * 7/1944 Krumboltz ............. B01J 19/087
204/155
2,607,807 A 8/1952 Ford
(Continued)

FOREIGN PATENT DOCUMENTS

JP 2001046874 A * 2/2001

OTHER PUBLICATIONS

Celanese patents acetic acid to ethanol conversion process, accessed at https://web.archive.org/web/20120605041308/http://www.biofuelsdigest.com/bdigest/2011/01/10/celanese-patents-acetic-acid-to-ethanol-conversion-process/, posted on Jan. 10, 2011, pp. 1-9.
(Continued)

*Primary Examiner* — Keith Hendricks
*Assistant Examiner* — Colleen M Raphael
(74) *Attorney, Agent, or Firm* — Pepper Hamilton LLP (57) ABSTRACT

Systems and methods are disclosed for synthesizing one or more simple alcohols from mixtures including organic acids, water, and a superparamagnetic catalyst exposed to fluctuating magnetic fields under ambient conditions.

8 Claims, 6 Drawing Sheets

(51) Int. Cl.
 B01J 35/00 (2006.01)
 C07C 29/00 (2006.01)
 C01G 49/00 (2006.01)
 B01J 23/78 (2006.01)
 B01J 19/00 (2006.01)

(52) U.S. Cl.
 CPC .......... *B01J 23/78* (2013.01); *B01J 35/0033* (2013.01); *C01G 49/0036* (2013.01); *C07C 29/00* (2013.01); *B01J 2219/0093* (2013.01); *B01J 2219/00792* (2013.01); *B01J 2219/00799* (2013.01); *B01J 2219/00835* (2013.01); *B01J 2219/00846* (2013.01); *B01J 2219/00905* (2013.01); *B01J 2219/00909* (2013.01); *B01J 2219/00952* (2013.01); *B01J 2219/00961* (2013.01); *B01J 2219/00963* (2013.01); *B01J 2219/0854* (2013.01); *B01J 2219/0866* (2013.01); *B01J 2219/0869* (2013.01); *B01J 2219/0877* (2013.01); *B01J 2219/0892* (2013.01); *B01J 2219/1945* (2013.01); *C01P 2004/64* (2013.01); *C01P 2006/42* (2013.01); *Y02P 20/52* (2015.11)

(58) Field of Classification Search
 CPC ............. C01G 49/0036; C01P 2004/64; C01P 2006/42
 USPC ...................................................... 204/157.9
 See application file for complete search history.

(56) References Cited

U.S. PATENT DOCUMENTS

| | | | |
|---|---|---|---|
| 4,517,391 A | 5/1985 | Schuster et al. | |
| 4,810,401 A * | 3/1989 | Mair .................. | A61K 49/1806 252/62.56 |
| 5,411,730 A * | 5/1995 | Kirpotin ............ | A61K 41/0052 252/62.56 |
| 5,763,353 A * | 6/1998 | Kadono ................ | B01J 23/005 502/329 |
| 7,863,489 B2 | 1/2011 | Johnston et al. | |
| 8,518,853 B2 * | 8/2013 | Kim ........................ | B01J 23/72 502/318 |
| 2002/0106314 A1* | 8/2002 | Pelrine ................. | B01J 19/0093 422/186 |
| 2003/0050516 A1* | 3/2003 | Fischer .................... | B01J 23/36 568/821 |
| 2004/0026028 A1* | 2/2004 | Kirsten .................... | H05B 6/80 156/272.4 |
| 2006/0102871 A1* | 5/2006 | Wang .................... | H01F 1/0063 252/62.51 R |
| 2007/0142648 A1* | 6/2007 | Urtel ....................... | C07B 41/02 548/571 |
| 2010/0197485 A1* | 8/2010 | Johnston ................ | B01J 23/002 502/241 |
| 2011/0263910 A1* | 10/2011 | Johnston ................ | C07C 29/149 568/885 |
| 2011/0282109 A1* | 11/2011 | Johnston ................ | C07C 29/149 568/885 |
| 2012/0030995 A1* | 2/2012 | Johnston ................ | C07C 29/149 560/265 |
| 2012/0253085 A1* | 10/2012 | Johnston ................ | C07C 29/149 568/885 |
| 2013/0345478 A1* | 12/2013 | Wollrab ................ | C07C 29/149 568/885 |

OTHER PUBLICATIONS

Ethanoic acid, accessed at https://web.archive.org/web/20120704080433/http://www.rod.beavon.clara.net/aceticac.htm, accessed on Jan. 14, 2015, pp. 1-4.
Infrared: Interpretation, accessed at https://web.archive.org/web/20120425224929/http://chemwiki.ucdavis.edu/Wikitexts/UCD_Chem_205:_Larsen/ChemWiki_Module_Topics/Infrared:_Interpretation, accessed on Jan. 14, 2015, pp. 1-26.
"Chemindustry", accessed at http://www.chemindustry.com/chemicals/26481.html, pp. 2, accessed on Mar. 2, 2017.
"Cost-saving measure to upgrade ethanol to butanol—a better alternative to gasoline," American Chemical Society (ACS), Apr. 11, 2013, accessed at www.sciencedaily.com/releases/2013/04/130411123500.htm, pp. 3, accessed on Mar. 17, 2017.
"O2-A2 Oxygen Sensor," accessed at http://apollounion.en.ec21.com/O2_A2_Oxygen_Sensor—5788327_5787965.html, accessed on Mar. 2, 2017, pp. 3.
Kao, W.C., et al., "Enhancing butanol production with Clostridium pasteurianum CH4 using sequential glucose-glycerol addition and simultaneous dual-substrate cultivation strategies," Bioresour Technology, vol. 135, pp. 324-330 (May 2013).
Sanchez, D.L.R., "Butanol Production From Glycerol by Clostridium Pasteurianum in Defined Culture Media—A Phenotypic Approach," Thesis submitted to the Faculty of the Graduate School of the University of Maryland, College Park, in partial fulfillment of the requirements for the degree of Master of Science, pp. 100 (2009).
Stombaugh, T., et al., "Butanol: The New Biofuel," Biosystems and Agricultural Engineering, pp. 2 (Mar. 2, 2017).
Wang, Y., et al., Tuning the Reactivity of Oxide Surfaces by Charge-Accepting Adsorbates, Angewandte Chemie, vol. 46, Issue 38, pp. 7315-7318 (Sep. 24, 2007).
Zhu, Y., and Jones, S.B., "Techno-economic Analysis for the Thermochemical Conversion of Lignocellulosic Biomass to Ethanol via Acetic Acid Synthesis," US department of Energy, pp. 79 (Apr. 2009).

* cited by examiner

METHODS, MATERIALS, AND SYSTEMS FOR CONVERTING ORGANIC ACIDS TO ALCOHOLS

CLAIM OF PRIORITY

This application claims priority benefit under 35 U.S.C. §119(a) of Indian Patent Application No. 1154/CHE/2014 filed Mar. 6, 2014, entitled "Methods, Materials, and Systems for Converting Organic Acids to Alcohols," the disclosure of which is herein incorporated by reference in its entirety.

BACKGROUND

Alcohols are important commodity feedstocks for a variety of industrial products, and ethanol, for example, is used as a fuel additive to gasoline. Further, ethanol can readily be dehydrated to ethylene, which in turn may be converted, for example, to useful polymer products. Processes exist to produce ethanol from the hydrogenation of acetic acid. In one such process, ethanol may be formed from an interaction of acetic acid with a ruthenium catalyst at pressures of about 70 MPa to about 95 MPa. Under such conditions, the yield of ethanol may be about 88%. At lower pressures of about 20 MPa, only about 40% yield of ethanol was obtained.

Another process was described for producing ethanol by hydrogenating acetic acid in the presence of a cobalt catalyst. The process may require pressures of about 4 MPa to about 12 MPa, although pressures of about 30 MPa may be required to improve ethanol percent yield. Further, the catalyst may require additional components such as copper, manganese, molybdenum, chromium, and phosphoric acid.

Both of these processes require expensive catalysts and high pressures for reasonable percent yields of ethanol. There is thus a need for a process that uses a cost-effective catalyst and can occur under reasonable conditions.

SUMMARY

For the purpose of this disclosure, a superparamagnetic nanoparticulate may be defined as a nanoparticle comprising a single magnetic domain having two stable and antiparallel magnetic moments, between which the material may transition at temperatures below the Curie temperature of the material.

In an embodiment, a method for synthesizing an alcohol may include contacting a carboxylic acid with water to form a first mixture, contacting the first mixture with a superparamagnetic catalyst to form a second mixture, and exposing the second mixture to a fluctuating magnetic field to form a third mixture thereby yielding the alcohol, in which the method is carried out at ambient conditions.

In an embodiment, a method for synthesizing an alcohol from a polyol may include contacting the polyol with water to form a first mixture, contacting the first mixture with a superparamagnetic catalyst to form a second mixture, and exposing the second mixture to a fluctuating magnetic field to form a third mixture thereby yielding the alcohol, in which the method is carried out at ambient conditions.

In an embodiment, a continuous or flow-through method for synthesizing an alcohol from a carboxylic acid may include contacting the carboxylic acid with water to form a first mixture, contacting the first mixture with a superparamagnetic catalyst to form a second mixture, and passing the second mixture through a fluctuating magnetic field to form a third mixture thereby yielding the alcohol, in which the method is carried out at ambient conditions.

In an embodiment, a continuous or flow-through method for synthesizing an alcohol from a polyol may include contacting the polyol with water to form a first mixture, contacting the first mixture with a superparamagnetic catalyst to form a second mixture, and passing the second mixture through a fluctuating magnetic field to form a third mixture thereby yielding the alcohol, in which the method is carried out at ambient conditions.

In an embodiment, a method for decomposing water may include contacting water with a superparamagnetic catalyst to form a first mixture and exposing the first mixture to a fluctuating magnetic field thereby yielding hydrogen gas and oxygen gas, in which the method is carried out at ambient conditions.

In an embodiment, a method of synthesizing a superparamagnetic catalyst may include contacting at least one salt of a ferromagnetic material in a strong base with at least one linking compound to form a first mixture, adding one or more paramagnetic salts to the first mixture to form a second mixture, heating the second mixture to form a pre-catalytic material, cooling and washing the pre-catalytic material, isolating the pre-catalytic material from the second mixture, and annealing the isolated pre-catalytic material to form the superparamagnetic catalyst.

In an embodiment, a continuous or flow-through system for synthesizing an alcohol using a superparamagnetic catalyst may include a reaction chamber adapted for fluid communication with a source of a reactant, water, and a superparamagnetic catalyst, and in fluid communication with an exit port, a pump in fluid communication with the reaction chamber, and a magnetic field generator located proximate the reaction chamber and adapted to create a fluctuating magnetic field within the reaction chamber.

In an embodiment, a composition may include a superparamagnetic catalyst in water.

In an embodiment, a method for synthesizing a thiol may include contacting a sulfonic acid with water to form a first mixture, contacting the first mixture with a superparamagnetic catalyst to form a second mixture, and exposing the second mixture to a fluctuating magnetic field to form a third mixture thereby yielding the thiol, in which the method is carried out at ambient conditions.

In an embodiment, method includes contacting an organic material with water to form a first mixture, contacting the first mixture with a superparamagnetic catalyst to form a second mixture, and exposing the second mixture to a fluctuating magnetic field to form a third mixture thereby yielding a hydroxylated derivative of the organic material, in which the method is carried out at ambient conditions.

DETAILED DESCRIPTION

Existing processes to synthesize alcohols, such as preparing ethanol from acetic acid, often require expensive catalysts, high pressures, or both. It may thus be recognized that a simple process that uses inexpensive and reusable chemicals under ambient conditions may be desirable.

The materials and processes disclosed herein may provide useful alternatives to the expensive catalysts and high-pressure reaction conditions otherwise available. In addition, the methods and materials disclosed below may be scalable to large and continuous production facilities because the synthesis processes may be run under ambient pressure and the catalyst may be synthesized from easily available materials.

Figure 1:
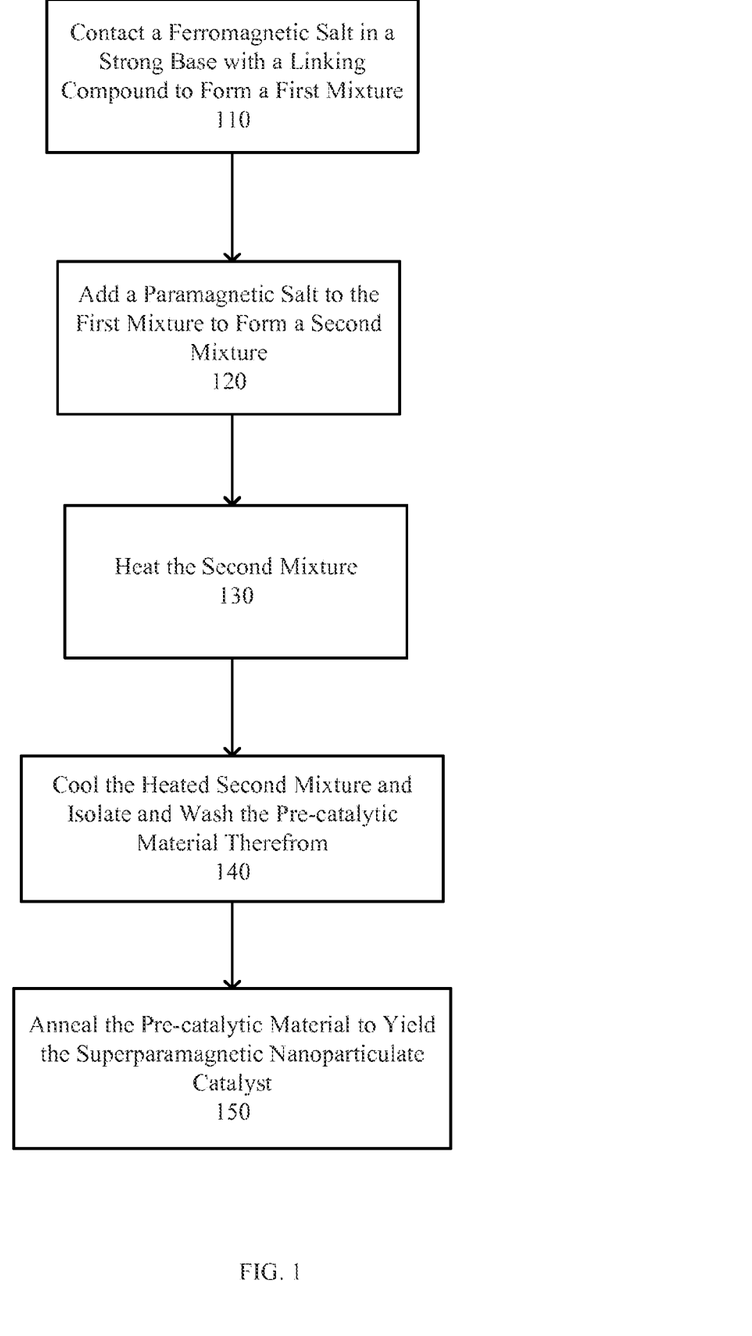
FIG. 1 is a flow diagram of a method for producing a superparamagnetic catalyst in accordance with some embodiments of the present disclosure.

Some methods for synthesizing an alcohol from a carboxylic acid, as disclosed herein, are based, at least in part, on exposing a mixture comprising a nanoparticulate ferromagnetic catalyst to a fluctuating magnetic field. FIG. 1 is a flow diagram of an embodiment of a method to synthesize such a superparamagnetic catalyst.

Generally, some methods of synthesizing a superparamagnetic catalyst may include contacting at least one salt of a ferromagnetic material in a strong base with at least one linking compound to form a first mixture 110, adding one or more paramagnetic salts to the first mixture to form a second mixture 120, heating the second mixture to form a pre-catalytic material 130, cooling and washing the pre-catalytic material, isolating the pre-catalytic material from the second mixture 140, and annealing the isolated pre-catalytic material to form the superparamagnetic catalyst 150. Each of these steps is discussed more fully below.

In a strong base, a salt of at least one ferromagnetic material contacts 110 a linking compound to form a first mixture. In some non-limiting embodiments, the strong base may comprise NaOH, LiOH, KOH, RbOH, CsOH, or combinations thereof. In some non-limiting examples, the strong base may generally have any concentration, such as about 5.5N to about 6.5N. In one non-limiting example, the strong base may be 6N NaOH. In some non-limiting embodiments, the salt of the ferromagnetic material may be a halide salt. Non-limiting examples of ferromagnetic materials may include iron, nickel, cobalt, gadolinium, dysprosium, or combinations thereof. One non-limiting example of a salt of a ferromagnetic material is ferric chloride. In some non-limiting embodiments, the linking compound may include one or more of an alkyl compound, an aryl compound, and a cyclo-alkyl compound, in which the linking compound further comprises at least a first functional group and a second functional group. The first functional group and the second functional group may be independently chosen from a thiol group, a hydroxyl group, an amine group, and an amide group.

In some non-limiting embodiments, the linking compound may be an α-hydroxy, ω-thiol alkyl compound. As one non-limiting example, the linking compound may be β-mercaptoethanol ($HOCH_2CH_2SH$). In the first mixture, the molar ratio of the salt of the ferromagnetic material to the linking compound may be about 0.5 to about 1. In one non-limiting example, the molar ratio of the salt of the ferromagnetic material to the linking compound may be about 1.

A second mixture may be formed by adding 120 at least one paramagnetic salt to the first mixture. The paramagnetic salt may include one or more of a halide and an oxide. Non-limiting examples of paramagnetic salts include magnesium, aluminum, titanium, manganese, molybdenum, tungsten, or combinations thereof. In one non-limiting example, the paramagnetic salt may be magnesium chloride. The weight ratio of the paramagnetic salt to the salt of the ferromagnetic material in the second mixture may be about 1. In one non-limiting embodiment, wherein adding 120 the one or more paramagnetic salts to the first mixture comprises adding a mixture of the one or more paramagnetic salts slowly to the first mixture, for example in a drop-wise fashion. In another non-limiting embodiment, adding 120 the one or more paramagnetic salts to the first mixture may comprise adding a mixture of the one or more paramagnetic salts continuously to the first mixture.

The second mixture may be heated 130 to form a pre-catalytic material. In one non-limiting embodiment, the second mixture may be heated 130 in an open container. In one non-limiting embodiment, the second mixture may be heated 130 by refluxing the second mixture. In yet another non-limiting embodiment, the second mixture may be heated 130 in a Soxhlet extractor. The second mixture may be heated 130 to an elevated temperature, such as a temperature of about 50 degrees C. to about 100 degrees C. In one embodiment, the second mixture may be heated 130 to about 100 degrees C. The second mixture may be heated 130 for generally any period of time, such as about 0.5 hours to about 1 hour. In one embodiment, the second mixture may be heated 130 for about 1 hour.

The second mixture may be cooled 140 and the pre-catalytic material may be isolated and washed 140. In one non-limiting example, the pre-catalytic material may be washed with distilled water, and the pH of the effluent may be monitored. The pre-catalytic material may be washed until the effluent has a pH of about 7.

The pre-catalytic material may be annealed 150 to yield the superparamagnetic catalyst. In one non-limiting embodiment, annealing 150 the pre-catalytic material may comprise heating the pre-catalytic material. As one non-limiting example, the pre-catalytic material may be heated in an oven to an elevated temperature, such as a temperature of about 50 degrees C. to about 70 degrees C. In an alternative non-limiting embodiment, the pre-catalytic material may be heated to a temperature of about 500 degrees C. to about 700 degrees C. in a furnace. As one non-limiting example, the pre-catalytic material may be heated to a temperature of about 500 degrees C. in a furnace. In yet another non-limiting example, the pre-catalytic material may be first heated in an oven at a temperature of about 50 degrees C. to about 70 degrees C. for about 15 minutes to about 30 minutes and, thereafter, may be heated in a furnace at about 500 degrees C. for about 15 minutes to about 20 minutes. In some non-limiting embodiments, the pre-catalytic material may be heated in an oxygen-deficient environment or an oxygen-free environment. One example of such oxygen-deficient environments may include a vacuum. Other examples of such oxygen-deficient environments may comprise, without limitation, carbon dioxide, nitrogen, helium, argon, and combinations thereof. The pre-catalytic material may be heated for generally any period of time, such as about 15 minutes to about 20 minutes. In one example, the pre-catalytic material may be heated for about 20 minutes.

As one non-limiting example, a superparamagnetic catalyst may be produced by the method disclosed in FIG. 1 in which the ferromagnetic salt is ferric chloride, the paramagnetic salt is magnesium oxide, and the linker material is β-mercaptoethanol. The superparamagnetic catalyst thus formed may be characterized by the formula $FeMgO_2$. In addition, the superparamagnetic catalyst thus formed may have an average particle diameter of about 25 nm to about 100 nm. Examples of such average diameter may include, without limitation, about 25 nm, about 30 nm, about 40 nm, about 50 nm, about 60 nm, about 70 nm, about 80 nm, about 90 nm, about 100 nm, and ranges between any two of these values (including endpoints).

Figure 2A:
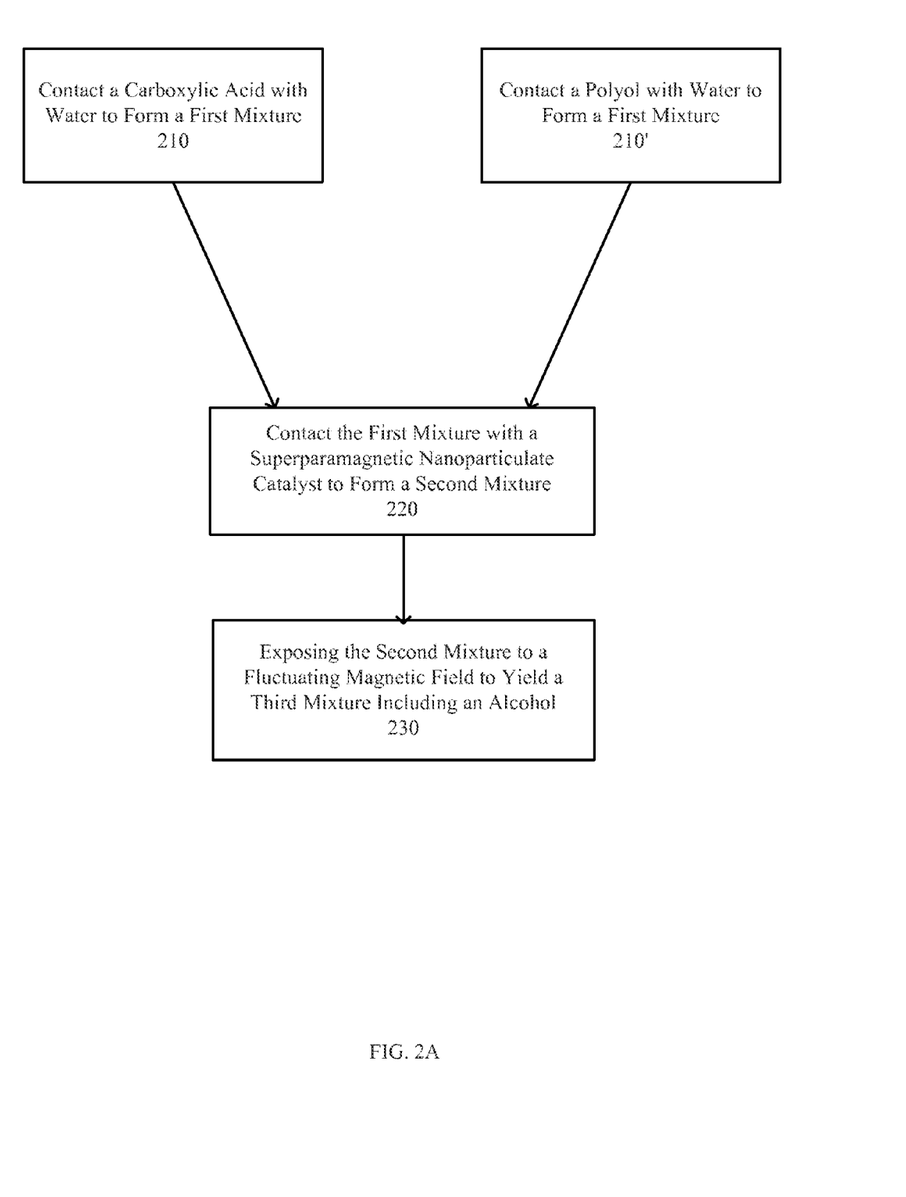
FIG. 2A is a flow diagram of a method for producing an alcohol from a carboxylic acid or a polyol in accordance with some embodiments of the present disclosure.

The superparamagnetic catalyst produced according to the method disclosed in FIG. 1 may be used in methods to convert materials into alcohols, as disclosed in FIG. 2A. It may be appreciated that the method steps disclosed in FIG. 2A (as well a companion FIG. 2B) all occur under ambient conditions of pressure (about 100 kPa) and temperature (around 25 degrees C.).

In one embodiment of the method as illustrated by the flow-diagram in FIG. 2A, a carboxylic acid may be contacted 210 with water to form a first mixture. In some non-limiting examples, the carboxylic acid may be formic acid, acetic acid, propionic acid, butyric acid, valeric acid, or combinations thereof. In other non-limiting embodiments, the carboxylic acid may comprise one or more dicarboxylic acids, including one or more α,ω-dicarboxylic acids. Some non-limiting examples of such α,ω-dicarboxylic acids may include malonic acid, succinic acid, glutaric acid, adipic acid, pimelic acid, or combinations thereof. The first mixture may have a molar ratio of water to the one or more carboxylic acids of about 1.2:1 to about 4:1. Non-limiting examples of the molar ratio of water to the one or more carboxylic acids may include 1.2:1, 1.5:1, 2:1, 2.5:1, 3:1, 3.5:1, 4:1, and ranges between any two of these values (including endpoints).

The first mixture may be contacted 220 with a superparamagnetic catalyst to form a second mixture. In some non-limiting examples, the superparamagnetic catalyst may comprise at least one ferromagnetic compound. In some non-limiting examples, the superparamagnetic catalyst may comprise at least one paramagnetic compound. In some alternative non-limiting examples, the superparamagnetic catalyst may comprise at least one ferromagnetic compound and at least one paramagnetic compound. As one non-limiting example, the ferromagnetic compound may include iron and the paramagnetic compound may include magnesium. Contacting 220 the superparamagnetic catalyst with the first mixture may result in a second mixture. As the superparamagnetic nanoparticulate comprises a catalyst, the amount of the catalyst in the second mixture may, in part, determine a catalytic reaction rate for the conversion of the acid to the alcohol. In one non-limiting example, the second mixture may comprise a weight:weight ratio the superparamagnetic catalyst to a carboxylic acid of about 3.75.

The second mixture may be exposed 230 to a fluctuating magnetic field, thereby forming a third mixture that may include one or more alcohols. In some non-limiting embodiments, the third mixture comprises the alcohol and the superparamagnetic catalyst. In some non-limiting embodiments, the fluctuating magnetic field may have a field strength of at least about 1 milliTesla. In some non-limiting embodiments, the fluctuating magnetic field may have a field strength of at least about 10 milliTesla. In one non-limiting example, the fluctuating magnetic field may have a field strength of about 1 milliTesla. It may be appreciated that the time for converting the one or more acids to the one or more alcohols may decrease with increasing fluctuating magnetic field strength. In some non-limiting embodiments, the fluctuating magnetic field may have a fluctuation frequency of about 10 Hz to about 2000 Hz. Some non-limiting examples of the magnetic field fluctuation frequency may be about 10 Hz, about 25 Hz, about 50 Hz, about 100 Hz, about 200 Hz, about 300 Hz, about 500 Hz, about 750 Hz, about 1000 Hz, about 1250 Hz, about 1500 Hz, about 1750 Hz, about 2000 Hz, and ranges between any two of these values (including endpoints). In one non-limiting example, the fluctuation frequency of the fluctuating magnetic field may be about 315 Hz. In another non-limiting example, the fluctuation frequency of the fluctuating magnetic field may be about 50 Hz. It may be appreciated that the time for converting the one or more acids to the one or more alcohols may decrease with increasing magnetic field fluctuation frequency. In some non-limiting examples, the fluctuating magnetic field may be supplied by an alternating current electromagnet. In some non-limiting embodiments, the second mixture may be exposed 230 to the fluctuating magnetic field for about 10 minutes to about 30 minutes. In some alternative non-limiting embodiments, the second mixture may be exposed 230 to the fluctuating magnetic field for generally any period of time, such as about 10 minutes to about 15 minutes. As one non-limiting example, the second mixture may be exposed 230 to the fluctuating magnetic field for about 30 minutes. Some non-limiting examples of the time during which the second mixture may be exposed 230 to the fluctuating magnetic field may be about 10 minutes, about 15 minutes, about 20 minutes, about 25 minutes, about 30 minutes, and ranges between any two of these values (including endpoints).

It may be appreciated that the type of alcohol formed and the percent yield of the alcohol in the third mixture may depend, at least in part, on the type of carboxylic acid and the molar ratio of water to the carboxylic acid in the first mixture. In one non-limiting example, the carboxylic acid may be acetic acid and the resulting alcohol may be ethanol. A percent yield of ethanol from acetic acid of about 75% to about 85% may result from a molar ratio of water to acetic acid in the first mixture of about 1.5:1 to about 2.5:1. In an alternative non-limiting example, the carboxylic acid may be acetic acid and the resulting alcohol may be methanol. A percent yield of methanol from acetic acid of about 50% to about 65% may result from a molar ratio of water to acetic acid in the first mixture of about 3:1 to about 4:1.

The superparamagnetic catalyst in the third mixture may be separated therefrom, leaving at least the alcohol. The superparamagnetic catalyst may be separated from the third mixture by one or more non-limiting methods including filtration, centrifugation, magnetic separation, or a combination thereof.

It may be understood that the steps disclosed in FIG. 2A represent only one non-limiting embodiment of the method. For example, a first mixture may comprise a ferromagnetic particulate catalyst in water, while a second mixture may comprise the first mixture to which a carboxylic acid may be added. While a third mixture, obtained by exposing 230 the second mixture to a fluctuating magnetic field, may comprise an alcohol and the ferromagnetic particulate catalyst, it may be understood that 100% yield of the alcohol may not always occur. As a result, some amount of water and unreacted carboxylic acid may also be included in the third mixture.

In addition to producing one or more alcohols from carboxylic acids, the ferromagnetic nanoparticulate catalyst may also be used to produce alcohols from polyols. In such a method, the first mixture may be formed by contacting 210' a polyol with water. As disclosed in FIG. 2A, this alternative first mixture may be contacted 220 with a superparamagnetic catalyst to form a second mixture. The polyol-containing second mixture may be exposed 230 to a fluctuating magnetic field to yield a third mixture that may comprise one or more alcohols. The method of converting at least a portion of a mixture containing one or more polyols and water into one or more alcohols may be performed under ambient conditions. In some embodiments, the polyol may comprise a vicinal polyol. In some non-limiting examples, the polyol may include ethylene glycol, propylene glycol, glycerol, or combinations thereof. In some embodiments, the third mixture may include methanol, ethanol, propanol, butanol, pentanol, or combinations thereof.

It may be appreciated that the superparamagnetic catalyst in the third mixture formed from a first mixture comprising at least one polyol may be separated therefrom according to methods and techniques disclosed above.

Figure 2B:
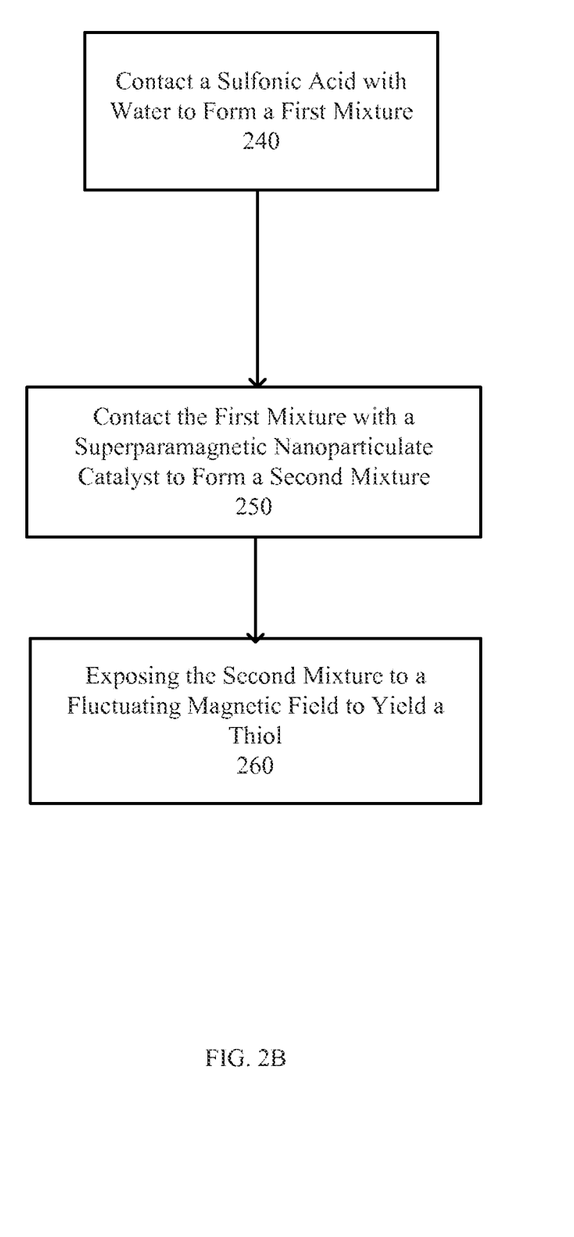
FIG. 2B is a flow diagram of a method for producing a thiol from a sulfonic acid in accordance with some embodiments of the present disclosure.

In another embodiment, FIG. 2B presents a flow-diagram of a method of forming one or more thiols from one or more sulfonic acids. A first mixture may be formed by contacting 240 a sulfonic with water. The first mixture may be contacted 250 with a superparamagnetic catalyst to form a second mixture. The second mixture may be exposed 260 to a fluctuating magnetic field to yield a third mixture that may comprise one or more thiols. Consist with the method disclosed above with respect to carboxylic acids and alcohols, the method of converting at least a portion of a mixture containing one or more sulfonic acids and water into one or more thiols may be performed under ambient conditions.

In still another embodiment, water may be decomposed into hydrogen gas and oxygen gas from a first mixture comprising water and a superparamagnetic catalyst. The hydrogen gas and oxygen gas may be formed by exposing the first mixture to a fluctuating magnetic field.

The embodiments of methods for synthesizing alcohols and thiols as disclosed above and depicted in FIGS. 2A and B may, in some designs, be implemented in a "one-pot" reaction system. In such a system, the acid, polyol, or sulfonic acid may be combined with water and the superparamagnetic catalyst in any order to form a mixture placed within a reaction chamber. The mixture within the reaction chamber may be exposed to a fluctuating magnetic field to produce a resultant mixture comprising the superparamagnetic catalyst and a product (such as an alcohol or thiol). Some amount of unreacted initial material, such as water, acid, polyol, or sulfonic acid, may remain in the resultant mixture. In a "one-pot" reaction system, the reaction chamber may comprise, for example, a beaker, a cylinder, or other container proximate to one or more sources of a fluctuating magnetic field. The geometry of the reaction chamber may be designed to expose essentially all of a mixture therein to the fluctuating magnetic field for the period of time during which the mixture is exposed to the magnetic field.

Alternatively, the methods disclosed above may be implemented in a continuous or "flow-through" reaction system. A flow-through reaction system may include a reaction chamber disposed to permit a flow of one or more mixtures therethrough. One or more sources of fluctuating magnetic fields may be proximal to the reaction chamber and may be disposed so that the one or more mixtures flowing through the reaction system may pass at least one time through the fluctuating magnetic field or fields. In some configurations, the one or more mixtures may circulate through the reaction chamber, the sources of fluctuating magnetic fields, or both, two or more times.

In one non-limiting example of a flow-through method, a first mixture may be formed by contacting one or more carboxylic acids with water. A second mixture may be formed by contacting the first mixture with a superparamagnetic catalyst. The second mixture may be exposed to at least one fluctuating magnetic field by passing the second mixture through the magnetic field, thereby forming an alcohol. The second mixture may be passed through the one or more fluctuating magnetic fields one time or multiple times. It may be appreciated that a similar flow-through method may be used with a first mixture including one or more polyols and water, and passing a second mixture including the one or more polyols, water, and a superparamagnetic catalyst through one or more fluctuating magnetic fields to yield a third mixture including one or more alcohols. It may also be appreciated that a similar flow-through method may be used to synthesize one or more thiols from a first mixture including water and one or more sulfonic acids. It is understood that an additional step of separating the superparamagnetic catalyst from the third mixture may be included in any of the above disclosed flow-through methods. In yet another embodiment of a flow-through method, a mixture of water and a superparamagnetic catalyst may be passed through one or more fluctuating magnetic fields to yield oxygen and hydrogen gas.

Figure 3A:
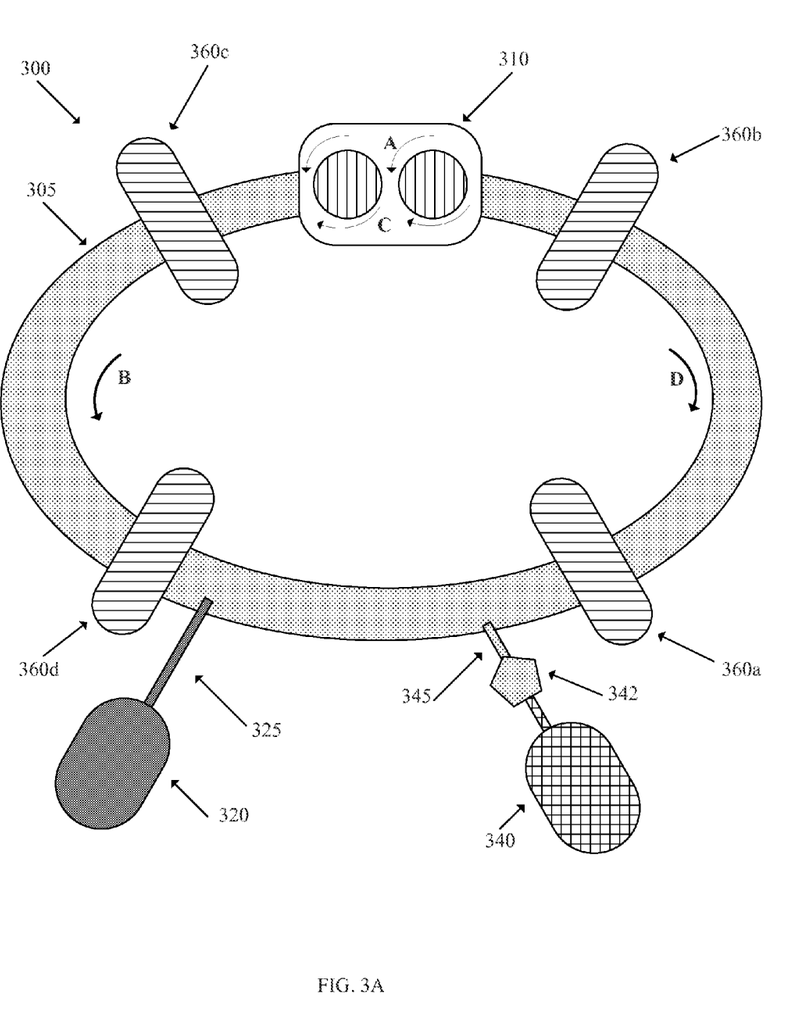
FIG. 3A is a schematic view of an embodiment of a circulating flow-through method of producing an alcohol from a mixture comprising a carboxylic acid or a polyol, water, and a superparamagnetic catalyst in accordance with some embodiments of the present disclosure.
Figure 3B:
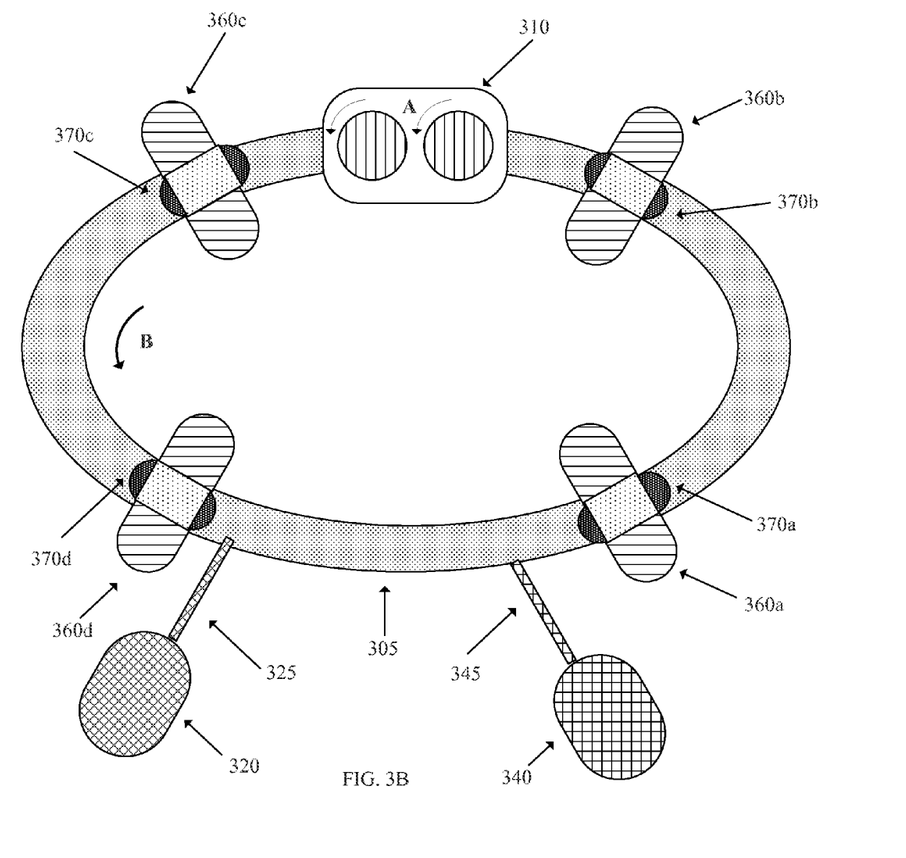
FIG. 3B is a schematic view of an embodiment of a circulating flow-through method of producing an alcohol from a carboxylic acid or a polyol, including a confined superparamagnetic catalyst in accordance with some embodiments of the present disclosure.

Non-limiting embodiments of flow-through systems that may be used with liquid mixtures including superparamagnetic catalysts are disclosed in FIGS. 3A-3B. While the embodiments disclosed may include different specific components, they all incorporate at least one reaction chamber in fluid communication with a source of a reactant, water, a superparamagnetic catalyst, and a mixture exit port. The systems also include at least one pump to move the reaction mixture through the one or more reaction chambers, and at least one magnetic field generator located proximate to the reaction chamber(s) and configured to create fluctuating magnetic fields within the reaction chamber. Pumps may include any of a number of fluid-moving pumps, including, without limitation, reciprocating pumps, piston pumps, syringe pumps, bellows pumps, and peristaltic pumps. While systems depicted in FIGS. 3A and 3B may not illustrate specific components, such as valves, valve and pump controllers, and process sensors for sensing process parameters such as temperature, pressure, and magnetic field strength, all such additional components required for the operation and control of such flow-through systems may be considered part of non-limiting embodiments of the systems presented in FIGS. 3A and 3B. Additionally, for the systems and methods disclosed below, it should be understood that references to "a carboxylic acid" as a reactant is purely a non-limiting example. Reactants including polyols or sufonic acids may be similarly subjected to the systems and methods disclosed below and in the figures.

FIG. 3A illustrates a non-limiting embodiment of a recirculating flow-through system 300. In the depicted embodiment of the recirculating flow-through system, the reaction chamber 305 may have a toroidal shape of any cross-sectional geometry in which the fluid may circulate due to the operation of a circulating pump 310. Multiple sources of fluctuating magnetic fields 360a-d may be in proximity to the reaction chamber 305. In some non-limiting examples, the sources of fluctuating magnetic fields 360a-d may comprise one or more solenoid magnets that may enclose one or more portions of the of the reaction chamber 305. In some non-limiting embodiments, each of the sources of fluctuating magnetic fields 360a-d may be controlled to provide about the same magnetic field strength. In some other non-limiting embodiments, the sources of fluctuating magnetic fields 360a-d may comprise a single source of a fluctuating magnetic field 360 that can surround nearly or completely the entire length of the reaction chamber 305. The single source of fluctuating magnetic fields 360 may be configured to produce an essentially uniform magnetic field along the length of the reaction chamber thus surrounded.

The circulating pump 310 may cause the fluid to flow in a path from a proximal side of the pump in fluid connection with a proximal end of the reaction chamber 305, through the reaction chamber to a distal end thereof in fluid connection with a distal end of the circulating pump. The path may be one or more of various shapes including, without limitation, a linear shape, a curved shape, a circular shape, an angular shape, and combinations thereof. The circulating pump 310, for example a peristaltic pump, may have components to rotate in a first direction (arrow A) that may result in the fluid in the recirculating flow-through system 300 to move in the direction indicated by arrow B. The circulating pump 300 may be controlled by a dedicated controller or may be controlled by a controller operating on any one or more of the other controllable components of the system. The controller of the circulating pump 300 may control the speed of the pump, the direction of the pump, or other parameters associated with pump control. In some non-limiting examples, the circulating pump 310 may operate in a single direction (arrow A) to cause the fluid within the reaction chamber 305 to move in a single direction (arrow B) through the one or more fluctuating magnetic fields supplied by fluctuating magnetic field sources 360a-d. In an alternative example, circulating pump 310 may be controlled to pump in a first direction (arrow A) followed by pumping in a second direction (arrow C), thereby circulating the fluid alternately in a first direction (arrow B) followed by a second direction (arrow D) through the one or more fluctuating magnetic fields supplied by fluctuating magnetic field sources 360a-d.

An input fluid may be supplied to the reaction chamber 305 from an input reservoir 320 through an inlet 325. One or more valves (not shown) may control the fluid flow into the reaction chamber 305. As disclosed above, water, one or more reactants (such as carboxylic acids, polyols, or sulfonic acids), and superparamagnetic catalysts may be introduced separately or as one or more combinations into the reaction chamber 305 from one or more input reservoirs 320 having separate or combined inlets 325. Upon one or more passes through the fluctuating magnetic fields produced by the one or more sources of fluctuating magnetic fields 360a-d, the product composition may be removed from the reaction chamber 305 into an output reservoir 340. The product composition may enter the output reservoir 340 via an outlet 345 controlled by the action of an output valve (not shown).

In one non-limiting example, the superparamagnetic catalyst may be introduced into the reaction chamber 305 and may circulate freely therethrough. The catalyst may be recovered by a separation device 342 when the product composition exits the reaction chamber 305. Examples of separation devices 342 may include, without limitation, a filter (physical separator) or a magnetic field (magnetic separator). Alternatively, the product composition, including the catalyst, may be retrieved in the output reservoir 340, and the catalyst may be removed in a subsequent step, for example by centrifugation.

FIG. 3B depicts an alternative non-limiting embodiment of a recirculating flow-through system. The recirculating flow-through system in FIG. 3B includes a reaction chamber 305 in a closed topology (for example a toroid) through which a fluid may flow along a continuous fluid circulation path under the actions of a circulating pump 310. An input fluid may be sourced by an input reservoir 320 through an inlet 325 into the reaction chamber 305. The fluid in the input reservoir 320 may comprise a reactant (such as a carboxylic acid, polyol, or sulfonic acid) along with water. Alternatively, the reactant may be sourced by a first reservoir and the water may be sourced by a second reservoir.

Figure 3C:
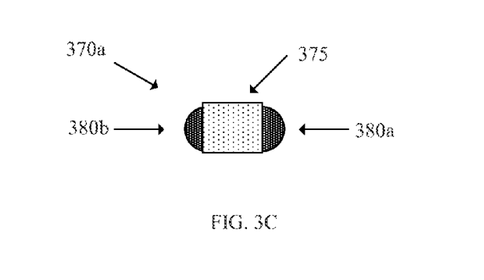
FIG. 3C is a schematic view of an embodiment of a confined superparamagnetic catalyst for an embodiment of a circulating flow-through method as depicted in FIG. 3B in accordance with some embodiments of the present disclosure.

The circulating pump 310 may operate in a first direction (arrow A) to circulate the fluid in a first direction (arrow B) through the reaction chamber 305. Although not depicted in FIG. 3B, it may be appreciated that the circulating pump 310 may also be controlled to alternate the direction of flow of the fluid through reaction chamber 305 analogous to the flow illustrated by arrows C and D in the equivalent embodiment depicted in FIG. 3A. The fluid in reaction chamber 305 may be circulated through one or more sources of fluctuating magnetic fields 360a-d. While FIG. 3A depicts a fluid comprising freely moving superparamagnetic catalysts, FIG. 3B illustrates an alternative embodiment in which the superparamagnetic catalysts may be confined to regions within the fluctuating magnetic fields as confined catalyst nanoparticles 370a-d. Thus, as non-limiting examples, confined catalyst nanoparticles 370a may be confined to a region experiencing the fluctuating magnetic field generated by the source 360a, confined catalyst nanoparticles 370b may be confined to a region experiencing the fluctuating magnetic field generated by source 360b, and similar for nanoparticles in 370c and source 360c, and nanoparticles in 370d and source 360d. In one non-limiting example, the superparamagnetic catalysts may be confined magnetically. In another non-limiting example, the superparamagnetic catalysts may be confined physically. In one non-limiting example, FIG. 3C illustrates a group of confined superparamagnetic catalysts 370a in a bolus 375 bounded on both sides by a porous barrier 380a,b. The porous barriers 380a,b may permit the fluid within the reaction chamber 305 to pass through the bolus 375 of superparamagnetic catalysts while maintaining the position of the catalyst nanoparticles within a fluctuating magnetic field. In an alternative example, an reaction chamber 305 may include structures, such as internal protrusions or fins, on which the catalyst nanoparticles may be immobilized.

Such a recirculating flow-through system as depicted in FIG. 3B may not require additional steps to remove the superparamagnetic catalysts from the product composition since the catalyst nanoparticle may not be freely circulating but may be localized within the reaction chamber 305.

Figure 4:
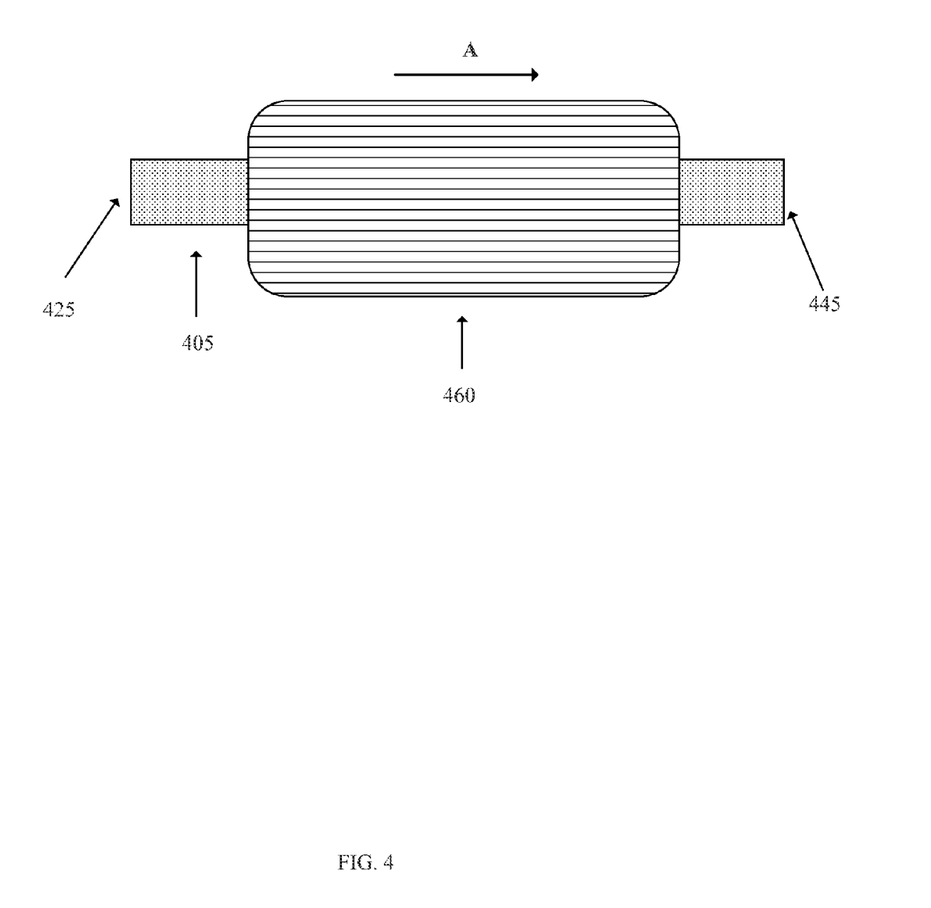
FIG. 4 is a schematic view of an embodiment of a continuous or flow-through method of producing an alcohol from a mixture comprising a carboxylic acid or a polyol, water, and a superparamagnetic catalyst in accordance with some embodiments of the present disclosure.

FIG. 4 illustrates another non-limiting example of a flow-through system. FIG. 4 illustrates an example of a single pass system comprising a reaction chamber 405 surrounded by at least one source of an alternating magnetic field 460. The reaction chamber 405 may include one or more straight segments, one or more curved segments, or combinations of straight and curved segments. The reaction chamber 405 may further have one or more cross-sectional shapes including, but not limited to, circular, oval, square, and rectangular cross-sectional shapes. In one non-limiting example, the reaction chamber 405 may be tubular. Although FIG. 4 illustrates a single source of an alternating magnetic field 460, it may be appreciated that one or more of such sources may be included in such a system. The one or more sources of an alternating magnetic field 460 may surround the reaction chamber 405 along any length or combination of lengths along the reaction chamber. In one non-limiting embodiment, a single source of an alternating magnetic field 460 may surround nearly all or all the length of the reaction chamber 405. In one non-limiting example, the reaction chamber 405 may be disposed along a longitudinal axis within a solenoid magnet (as a source of the alternating magnetic field 460). Such a single source of an alternating magnetic field 460 may be configured to deliver an essentially uniform fluctuating magnetic field along the length of the reaction chamber 405 surrounded thereby.

While FIGS. 3A and 3B may illustrate non-limiting examples of recirculating flow-through systems, FIG. 4 may illustrate, as one non-limiting example, a non-recirculating flow-through system. In an example of a non-recirculating flow-through system, one or more input fluids may be introduced into a first end of the reaction chamber 405 through one or more inlets 425 and flow along the length of the reaction chamber in a direction A. A product composition may be removed from the reaction chamber through one or more outlets 445 at a second end of the reaction chamber.

In one non-limiting embodiment, the one or more input fluids may include the superparamagnetic catalyst, which may flow freely along the length of the reaction chamber 405. The product composition may include the superparamagnetic catalyst as a component, and the superparamagnetic catalyst may be removed from the product composition by one or more of filtration, magnetic separation, or other methods. Such methods may include the use of one or more separation devices as illustrated in FIG. 3A, 342.

In an alternative non-limiting embodiment, the superparamagnetic catalyst may be confined to one or more regions within the fluctuating magnetic field as confined catalyst nanoparticles. Thus, as a non-limiting example, confined catalyst nanoparticles may be confined to a region experiencing the fluctuating magnetic field generated by the source 460. The superparamagnetic catalysts may be confined magnetically, physically, or by one or more additional mechanisms, as disclosed above in reference to FIGS. 3B and 3C.

Although non-limiting examples of methods and systems disclosed above are directed to the formation of alcohols or thiols from organic acids and sulfonic acids, respectively, the superparamagnetic catalyst so disclosed may generally be used to convert other organic species into hydroxylated derivatives. Such organic species may include functional groups including, but not limited to, a —C—C— group, a —C—H group, a —C—O— group, a —C—OH group, and a —OH group A general method for synthesizing such hydroxilated compounds may include contacting an organic material with water to form a first mixture, contacting the first mixture with a superparamagnetic catalyst to form a second mixture, and exposing the second mixture to a fluctuating magnetic field to form a third mixture comprising at least in part a hydroxylated derivative of the organic material. As disclosed above with respect to the other reactions, such a method may be carried out at ambient conditions.

EXAMPLES

Example 1

A Method of Making a Superparamagnetic Catalyst

A first mixture was made by dissolving 2 g of $FeCl_3$ in 30 ml of 6N NaOH under continuous stirring. To the first mixture was added 20 ml of a 5% by volume mixture of β-mercaptoethanol($HOCH_2CH_2SH$) in water to form a second mixture. To the second mixture was added 2 g of $MgCl_2$ under continuous stirring conditions to form a third mixture. The third mixture was refluxed in a soxhlet extractor at about 100 degrees C. for about 30 minutes to about 60 minutes to produce a pre-catalytic material. The pre-catalytic material was isolated, cooled, and washed with distilled water until the effluent had a pH of about 7. The pre-catalytic material was annealed in a furnace at about 500 degrees C. for about one hour to yield the superparamagnetic catalyst, $FeMgO_2$.

Example 2

A Method of Making an Alcohol from Acetic Acid

In a reaction chamber, purified water and glacial acetic acid were added in a molar ratio of 2:1 to form 6.5 ml of a first mixture. A second mixture was formed by adding 15 mg of an $FeMgO_2$ catalyst to the first mixture. The second mixture within the reaction chamber was placed in a source of a fluctuating magnetic field. The source of the fluctuating magnetic field was composed of a solenoid having a 110 mm outer diameter, a 58 mm inner diameter, and a 30 mm width. The solenoid was composed of 1045 turns of 18 gauge copper wire. A fluctuating magnetic field was generated by the solenoid magnet by introducing an AC current of 250 mA at a frequency of 315.8 Hz through the wiring. The second mixture was exposed to the fluctuating magnetic field for about 10 minutes to about 15 minutes to form the third mixture. The rate of conversion of the acid to the alcohol increased with increased current through the solenoid wires or with increased frequency of the current flow.

The type of alcohol produced was dependent on the molar ratio of water to acid as illustrated in Table 1.

TABLE 1

| Water In ml | Acetic acid In ml | Water:Acid Molar ratio | Titration color Observation | Ethanol/ Methanol/ Acetic acid |
|---|---|---|---|---|
| 4 | 4 | 3.2 | Transparent | Methanol |
| 3.5 | 4 | 2.8 | Transparent | Methanol |
| 2.5 | 4 | 2.0 | Yellow (mild) | Ethanol |
| 2 | 4 | 1.6 | Yellow (strong) | Ethanol |
| 1.5 | 4 | 1.2 | Yellow (mild) | Ethanol |
| 1 | 4 | 0.8 | Yellowish-light green | Acetic acid |
| 0.5 | 4 | 0.4 | green | Acetic acid |

In Table 1, each sample comprising the listed volumes of water and acetic acid plus 15 mg of the catalyst was exposed to a 1 mT 50 Hz magnetic field for about 30 minutes. Acid or alcohol content of the resultant composition was determined based on the iodoform colorimetric reaction in which a yellow color is indicative of ethanol. Methanol does not give a positive reaction to the test, resulting in a clear solution. Table 1 indicates that a water:acid molar ratio below about 1 may not be effective to convert acetic acid to an alcohol. A water:acid molar ration of about 1 to about 2 appears to lead preferentially to the formation of ethanol. A water:acid molar ration of about 2 to about 4 appears to lead preferentially to the formation of methanol. The reaction time may be adjusted according to the field strength and/or frequency of the fluctuating magnetic field. Thus, the reaction time may be reduced by increasing the field strength in the solenoid, for example by energizing the solenoid at higher voltages or currents. Similarly, increased field fluctuation frequency may also decrease the reaction time.

Example 3

A Method of Making an Alcohol from Glycerol

About 500 milligrams of the superparamagnetic catalyst was combined with a first mixture having a molar ration of water to glycerol of about 2:1 to form a second mixture. A solenoid system for producing a fluctuating magnetic current similar to that disclosed above in Example 2 was provided. The solenoid was energized at to provide a magnetic field strength of 1 mT at a frequency of 50 Hz, and the second mixture was exposed to the fluctuating magnetic field for about 30 minutes.

Example 4

A Method of Generating Hydrogen from Water

Water may be decomposed to form hydrogen and oxygen gases in the presence of the superparamagnetic catalyst and fluctuating magnetic field. The hydrogen gas thus generated may be used in industrial applications including, but not limited to, charging hydrogen fuel cells. In one example, about 500 mg of the catalyst was added to about 4 ml of purified water. The water plus catalyst mixture was exposed to a fluctuating magnetic field generated by a solenoid magnet in the manner disclosed in Example 3, above. Water decomposition provides gaseous hydrogen and oxygen in a stoichiometric ratio. Table 2 discloses an amount of oxygen generated by the mixture over time during the application of the fluctuating magnetic field to the water/catalyst mixture. The oxygen measurement can be used to infer an amount of hydrogen co-produced during the decomposition process.

TABLE 2

| Time (min) | Oxygen Concentration (%) |
|---|---|
| 0 | 21 |
| 15 | 26 |
| 30 | 33 |
| 15 | 40 |
| 60 | 44 |

Table 2 depicts an approximately linear relationship between the amount of oxygen generated by the system and the length of exposure time of the catalyst to the fluctuating magnetic field. It may be appreciated that the 21% oxygen concentration at zero time represents the amount of dissolved oxygen in the water before the application of the field. The use of the catalyst in conjunction with the fluctuating magnetic field may prove to be an improvement over DC electrolysis of water for generating hydrogen gas. Pure water contains a low concentration of dissolved charge carriers ($H^+$ and $OH^-$) and therefore requires a high DC potential (above the half-cell potentials for hydrogen and oxygen) to increase the concentration of charge carriers leading to water decomposition. The addition of salts, acids, or bases to pure water to increase the charge carrier concentration may lead to unwanted side reactions. Examples of such side reactions may include the generation of additional gases (for example, chlorine if HCl is added) with or instead of the hydrogen gas. The method disclosed above, comprising exposing water in combination with a re-usable catalyst to a fluctuating magnetic field, may prove a more energy efficient method to generate hydrogen gas than DC electrolysis methods since unwanted side reactions are avoided.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity.

It will be understood by those within the art that, in general, terms used in this disclosure, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A method for synthesizing an alcohol, the method comprising:
    contacting a carboxylic acid with water to form a first mixture;
    contacting the first mixture with a superparamagnetic catalyst to form a second mixture, wherein the superparamagnetic catalyst comprises at least one ferromagnetic compound and at least one paramagnetic compound; and
    exposing the second mixture to a fluctuating magnetic field to form a third mixture thereby yielding the alcohol,
    wherein the method is carried out at ambient conditions.

2. The method of claim 1, wherein contacting a carboxylic acid with water comprises contacting acetic acid with water, and
    wherein yielding the alcohol comprises yielding one of ethanol or methanol.

3. The method of claim 1, wherein contacting a carboxylic acid with water comprises contacting a dicarboxylic acid with water.

4. The method of claim 1, wherein contacting a carboxylic acid with water to form a first mixture comprises contacting the carboxylic acid with water to form the first mixture having a molar ratio of water to the carboxylic acid of about 1.5:1 to about 4:1.

5. The method of claim 1, wherein yielding of the alcohol depends at least in part on the carboxylic acid and a molar ratio of water to the carboxylic acid.

6. The method of claim 1, wherein exposing the second mixture to a fluctuating magnetic field comprises exposing the second mixture the fluctuating magnetic field having a field strength of at least about 1 milliTesla.

7. The method of claim 1, wherein exposing the second mixture to a fluctuating magnetic field comprises exposing the second mixture to the fluctuating magnetic field having a fluctuation frequency of about 10 Hz to about 2000 Hz.

8. The method of claim 1, wherein exposing the second mixture to a fluctuating magnetic field comprises exposing the second mixture to the fluctuating magnetic field for about 10 minutes to about 30 minutes.

\* \* \* \* \*

UNITED STATES PATENT AND TRADEMARK OFFICE
CERTIFICATE OF CORRECTION

PATENT NO. : 9,862,663 B2  
APPLICATION NO. : 14/640465  
DATED : January 9, 2018  
INVENTOR(S) : Thevasahayam Page 1 of 1

It is certified that error appears in the above-identified patent and that said Letters Patent is hereby corrected as shown below:

In the Specification

In Column 7, Line 11, delete "nanopoarticulate" and insert -- nanoparticulate --, therefor.

In Column 8, Lines 63-64, delete "sufonic" and insert -- sulfonic --, therefor.

In Column 9, Lines 31-32, delete "circulating pump 300" and insert -- circulating pump 310" --, therefor.

In Column 9, Line 35, delete "circulating pump 300" and insert -- circulating pump 310" --, therefor.

In Column 10, Lines 46-47, delete "catalysts 370a in" and insert -- catalysts in --, therefor.

In Column 10, Line 52, delete "example, an reaction" and insert -- example, the reaction --, therefor.

In Column 11, Line 58, delete "group A" and insert -- group. A --, therefor.

In Column 12, Line 67, delete "molar ration" and insert -- molar ratio --, therefor.

In Column 13, Line 2, delete "molar ration" and insert -- molar ratio --, therefor.

In Column 13, Line 16, delete "molar ration" and insert -- molar ratio --, therefor.

In Column 14, Line 54, delete "recitation no" and insert -- recitation, no --, therefor.

In Column 15, Line 9, delete "general such" and insert -- general, such --, therefor.

In the Claims

In Column 16, Line 35, in Claim 6, delete "mixture the" and insert -- mixture to the --, therefor.

Signed and Sealed this  
First Day of May, 2018

Andrei Iancu  
*Director of the United States Patent and Trademark Office*